(12) United States Patent
Nishio et al.

(10) Patent No.: US 9,696,477 B2
(45) Date of Patent: Jul. 4, 2017

(54) LIGHT SOURCE SYSTEM

(71) Applicant: OLYMPUS CORPORATION, Tokyo (JP)

(72) Inventors: Masahiro Nishio, Hachioji (JP); Takeshi Ito, Hino (JP); Eiji Yamamoto, Musashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 377 days.

(21) Appl. No.: 14/331,491

(22) Filed: Jul. 15, 2014

(65) Prior Publication Data

US 2014/0328063 A1 Nov. 6, 2014

Related U.S. Application Data

(63) Continuation of application No. PCT/JP2013/050830, filed on Jan. 17, 2013.

(30) Foreign Application Priority Data

Jan. 19, 2012 (JP) .................................. 2012-009221

(51) Int. Cl.
*F21V 1/00* (2006.01)
*F21V 11/00* (2015.01)
(Continued)

(52) U.S. Cl.
CPC ........ *G02B 6/0005* (2013.01); *A61B 1/00126* (2013.01); *A61B 1/0669* (2013.01);
(Continued)

(58) Field of Classification Search
CPC .. G02B 6/3825; G02B 6/0005; G02B 6/0006; G02B 6/4292; G02B 6/3895;
(Continued)

(56) References Cited

U.S. PATENT DOCUMENTS 6,331,156 B1 12/2001 Haefele et al.
6,602,186 B1 8/2003 Sugimoto et al.
(Continued)

FOREIGN PATENT DOCUMENTS

CN 1788673 A 6/2006
CN 101027520 A 8/2007
(Continued)

OTHER PUBLICATIONS

Machine translation of Kami, JP 2007-014423A, published Jan. 25, 2007.*
(Continued)

*Primary Examiner* — Peggy Neils
*Assistant Examiner* — William N Harris
(74) *Attorney, Agent, or Firm* — Scully, Scott, Murphy & Presser, P.C.

(57) ABSTRACT

A light source system includes an intermediary adapter which mechanically connects a first light source module, a first irradiation module, a second light source module and a second irradiation module, a first connection mechanism which connects the first light source module and the intermediary adapter and a second connection mechanism which connects the second light source module and the intermediary adapter. The first irradiation module and the second irradiation module are interchangeably connected to the intermediary adapter in the same plane of the intermediary adapter.

19 Claims, 6 Drawing Sheets (51) Int. Cl.
*G02B 6/26* (2006.01)
*G02B 6/42* (2006.01)
*F21V 8/00* (2006.01)
*A61B 1/00* (2006.01)
*A61B 1/07* (2006.01)
*A61B 1/06* (2006.01)
*G02B 6/38* (2006.01)

(52) U.S. Cl.
CPC .............. *A61B 1/07* (2013.01); *G02B 6/0006* (2013.01); *G02B 6/3825* (2013.01); *G02B 6/0008* (2013.01); *G02B 6/3895* (2013.01); *G02B 6/4292* (2013.01); *G02B 6/4298* (2013.01); *G02B 2006/4297* (2013.01)

(58) Field of Classification Search
CPC  G02B 6/3839; G02B 6/4214; A61B 1/00126; A61B 1/0669; A61B 1/07
USPC ............................................. 362/238; 385/44
See application file for complete search history.

(56) References Cited

U.S. PATENT DOCUMENTS

| | | | |
|---|---|---|---|
| 7,179,222 B2* | 2/2007 | Imaizumi | A61B 1/00009 600/109 |
| 2007/0189352 A1 | 8/2007 | Nagahama et al. | |
| 2009/0306478 A1* | 12/2009 | Mizuyoshi | A61B 1/0638 600/178 |
| 2010/0254153 A1 | 10/2010 | Hama et al. | |
| 2011/0172492 A1 | 7/2011 | Erikawa | |
| 2012/0215066 A1* | 8/2012 | Akiyama | A61B 1/00009 600/109 |
| 2014/0293651 A1* | 10/2014 | Ito | A61B 1/0669 362/613 |

FOREIGN PATENT DOCUMENTS

| | | |
|---|---|---|
| EP | 2 283 769 A1 | 2/2011 |
| JP | 2006-296636 A | 11/2006 |
| JP | 2007-014423 A | 1/2007 |
| JP | 2007-220326 A | 8/2007 |
| JP | 2011-156339 A | 8/2011 |

OTHER PUBLICATIONS

Extended Supplementary European Search Report dated Sep. 1, 2015 from related European Application No. 13 73 8188.5.
Chinese Office Action dated May 21, 2015 from related Chinese Application No. 201380004976.X, together with an English language translation.
English abstract of Japanese Patent Application No. JP 2006-173324.
English translation of the International Preliminary Report on Patentability dated Jul. 31, 2014, together with a Written Opinion received in related International Application No. PCT/JP2013/050830.
International Search Report dated Apr. 23, 2013 issued in PCT/JP2013/050830.

* cited by examiner

LIGHT SOURCE SYSTEM

CROSS-REFERENCE TO RELATED APPLICATIONS

This application is a Continuation application of PCT Application No. PCT/JP2013/050830, filed Jan. 17, 2013 and based upon and claiming the benefit of priority from prior Japanese Patent Application No. 2012-009221, filed Jan. 19, 2012, the entire contents of all of which are incorporated herein by reference.

BACKGROUND OF THE INVENTION

1. Field of the Invention

The present invention relates to a light source system having an intermediary adapter.

2. Description of the Related Art

For example, Jpn. Pat. Appln. KOKAI Publication No. 2007-220326 has disclosed a luminescent device. This luminescent device includes a first light source module having a laser light source, and a first irradiation module having a light guide and a wavelength converting member. Laser light is emitted from the laser light source and then guided to a distal end portion of the light guide. The wavelength of the laser light is then converted by the wavelength converting member provided at the distal end portion of the light guide.

In Jpn. Pat. Appln. KOKAI Publication No. 2007-220326, when the luminescent device further includes a second light source module having a lamp light source, the luminescent device needs to include a second irradiation module corresponding to the second light source module. Thus, as the number of light source modules and irradiation modules increases in accordance with the kinds of light to be used, so too do problems encountered by users in assembling the luminescent device, as they may be unable to accurately and easily assemble the luminescent device.

The present invention has been made under these circumstances, and an object of the invention is to provide a light source system which can be accurately and easily assembled regardless of the kind of irradiation module.

BRIEF SUMMARY OF THE INVENTION

An aspect of a light source system of the present invention includes a first light source module which emits first light source light; a second light source module which emits second light source light; a first irradiation module which functions by receiving the first light source light; a second irradiation module which functions by receiving the second light source light; an intermediary adapter, the intermediary adapter optically connecting the first light source module and the first irradiation module to each other, optically connecting the second light source module and the second irradiation module to each other, and mechanically connecting the first irradiation source module or the second irradiation source module to the first light source module and the second light source module; a first connection mechanism which connects the first light source module and the intermediary adapter to each other; and a second connection mechanism which connects the second light source module and the intermediary adapter to each other, wherein the intermediary adapter comprises a first light guide member which optically connects the first light source module and the first irradiation module to each other and which guides the first light source light from the first light source module to the first irradiation module, and a second light guide member which optically connects the second light source module and the second irradiation module to each other and which guides the second light source light from the second light source module to the second irradiation module, and the first irradiation module and the second irradiation module are interchangeably connected to the intermediary adapter in the same plane of the intermediary adapter.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described in detail with reference to the drawings.

First Embodiment

[Configuration]

A first embodiment is described with reference to FIG. 1.

[Light Source System 10]

Figure 1:
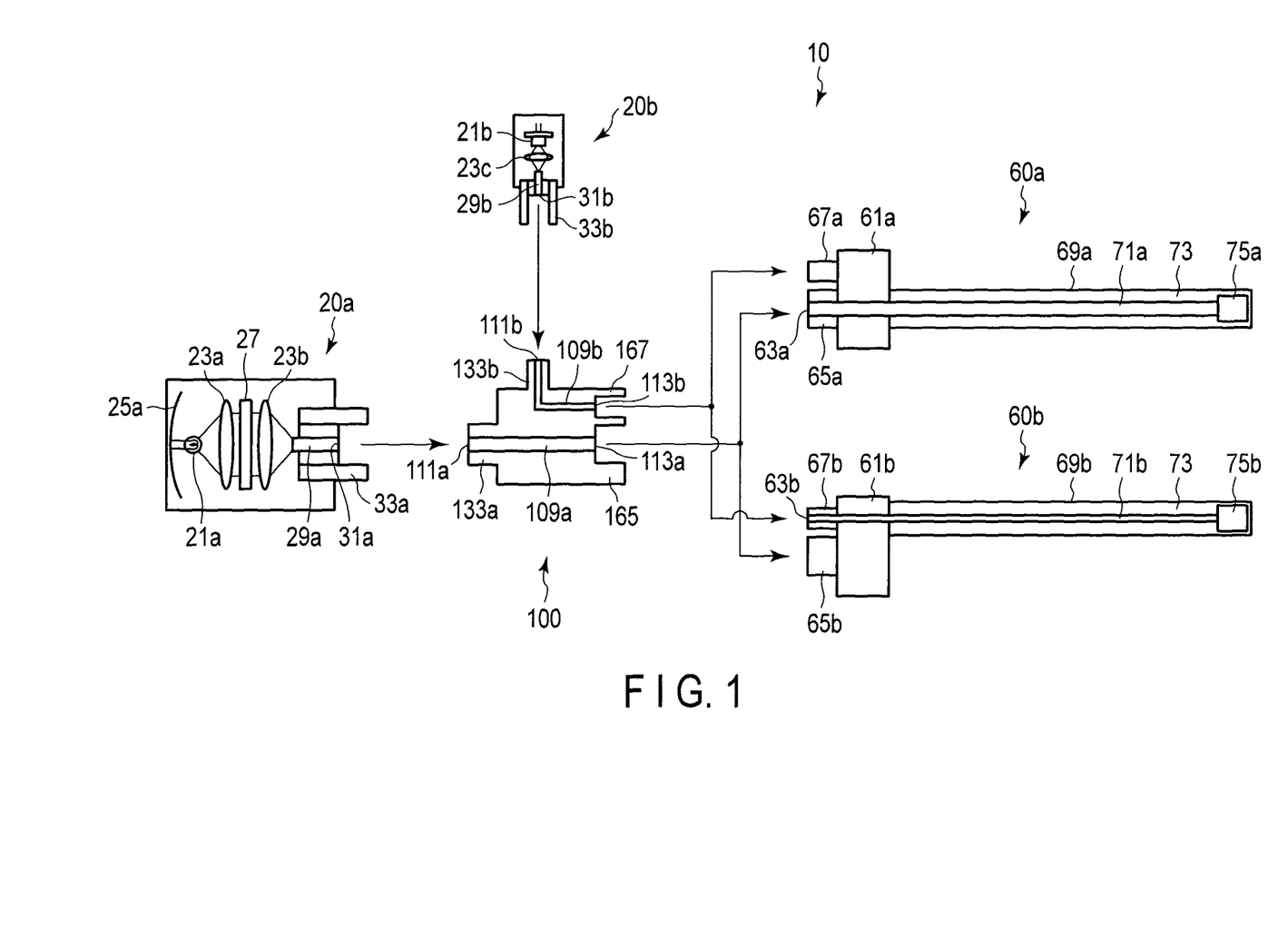
FIG. 1 is a schematic diagram of a light source system according to a first embodiment of the present invention.

As shown in FIG. 1, a light source system 10 includes a first light source module 20a which emits first light source light, a second light source module 20b which emits second light source light, a first irradiation module 60a which functions by receiving the first light source light, and a second irradiation module 60b which functions by receiving the second light source light. As shown in FIG. 1, the light source system 10 further includes an intermediary adapter 100 which optically connects the first light source module 20a and the first irradiation module 60a to each other, optically connects the second light source module 20b and the second irradiation module 60b to each other, and mechanically connects the first irradiation module 60a or the second irradiation module 60b to the first light source module 20a and the second light source module 20b. The first light source module 20a, the second light source module 20b, the first irradiation module 60a, the second irradiation module 60b, and the intermediary adapter 100 are separate from one another.

[First Light Source Module 20a]

As shown in FIG. 1, the first light source module 20a has a first light source 21a which emits the first light source light, and two lenses 23a and 23b which condense the first light source light emitted forward from the first light source 21a. As shown in FIG. 1, the first light source module 20a also has a mirror 25a which reflects forward the first light source light emitted rearward from the first light source 21a, a filter 27 which is provided between the two lenses 23a and 23b and which removes unnecessary components from the first light source light, and a light guide member 29a which guides the first light source light condensed by the lens 23b.

Here, "forward" signifies the front side in the traveling direction of the first light source light, and "rearward" signifies the rear side in the traveling direction of the first light source light.

The first light source 21a is, for example, a white light source. The first light source 21a is, for example, an electric discharge type lamp light source. More specifically, the first light source 21a is a xenon lamp which is a kind of electric discharge lamp. In this case, the first light source light is lamp light.

The first light source 21a may be, for example, a semiconductor light source such as an LED light source, or a filament-type lamp light source. Thus, the first light source 21a has only to have at least one of the LED light source and the lamp light source.

The lens 23a provided on the side of the first light source 21a converts the first light source light emitted from the first light source 21a to substantially parallel light.

The mirror 25a has a concave surface which condenses the first light source light to the lens 23a.

The filter 27 removes unnecessary ultraviolet and infrared components from the first light source light. The filter 27 is formed by, for example, a band pass filter, or by a combination of a low pass filter and a high pass filter.

The lens 23b provided on the side of the light guide member 29a condenses, to the light guide member 29a, the first light source light from which the unnecessary components have been removed by the filter 27.

Some of the first light source light is emitted toward the lens 23a from the first light source 21a. Some of the first light source light is emitted toward the mirror 25a from the first light source 21a. The rest of the first light source light is reflected toward the lens 23a by the mirror 25a. The first light source light is converted to parallel light by the lens 23a, and remove the ultraviolet component and the infrared component by the filter 27. The first light source light is then condensed to the light guide member 29a by the lens 23b, and incidences the light guide member 29a.

The light guide member 29a has a light guide rod which guides, to a later-described emission end portion 31a, the first light source light condensed by the lens 23b. The light guide member 29a has a large incidence region.

As shown in FIG. 1, the first light source module 20a further has the emission end portion 31a which is provided at the end portion of the light guide member 29a and which emits the first light source light, a fixing portion 33a which fixes the emission end portion 31a to an incidence end portion 111a provided in the intermediary adapter 100 so that the emission end portion 31a and the incidence end portion 111a are optically connected to each other, and an unshown heat radiation mechanism which radiates heat generated from the first light source module 20a.

The emission end portion 31a constitutes a first light source emission end portion which emits the first light source light and which is provided in the first light source module 20a. The emission end portion 31a is optically connectable to the incidence end portion 111a. The emission end portion 31a is formed as a large emission region.

The fixing portion 33a has a concave shape, and is provided around the emission end portion 31a. The fixing portion 33a constitutes a first light source side connection portion in which the emission end portion 31a is provided and which is provided in the first light source module 20a. The fixing portion 33a is fitted to a convex fixing portion 133a provided in the intermediary adapter 100. When the fixing portion 33a is fitted to the fixing portion 133a, the first light source module 20a is mechanically and optically connected to the intermediary adapter 100. Thus, the fixing portion 33a and the fixing portion 133a function as a first connection mechanism.

The heat radiation mechanism has, for example, a cooling fan and a heat radiation fan. The heat radiation mechanism radiates heat generated from the first light source 21a, and heat of a member which has increased in temperature by the application of the first light source light. This member is, for example, the mirror 25a.

[Second Light Source Module 20b]

As shown in FIG. 1, the second light source module 20b has a second light source 21b which emits the second light source light, a lens 23c which condenses the second light source light emitted from the second light source 21b, and a light guide member 29b which guides the second light source light condensed by the lens 23c.

The second light source 21b has, for example, an InGaN-based blue semiconductor laser which emits, for example, blue laser light as the second light source light. The laser light has a wavelength of, for example, 370 nm to 500 nm. A light emission point of the second light source 21b is small. Most of the laser light incidences the light guide member 29b due to the lens 23c.

The second light source 21b may have a superluminescent diode (SLD) which emits superluminescent light, or various laser light sources. Thus, the second light source 21b has only to have at least one of the laser light source and the superluminescent light source.

The light guide member 29b has an optical fiber which guides, to a later-described emission end portion 31b, the second light source light condensed by the lens 23c. The light guide member 29b is, for example, a laser light guiding optical fiber. The light guide member 29b has a small incidence region.

As shown in FIG. 1, the second light source module 20b further has the emission end portion 31b which is provided at the end portion of the light guide member 29b and which emits the second light source light, a fixing portion 33b which fixes the emission end portion 31b to an incidence end portion 111b so that the emission end portion 31b and the incidence end portion 111b provided in the intermediary adapter 100 are optically connected to each other, and an unshown heat radiation mechanism which radiates heat generated from the second light source module 20b.

The emission end portion 31b constitutes a second light source emission end portion which emits the second light source light and which is provided in the second light source module 20b. The emission end portion 31b is optically connectable to the incidence end portion 111b. The emission end portion 31b is formed as a small emission region.

The fixing portion 33b has a concave shape, and is provided around the emission end portion 31b. The fixing portion 33b constitutes a second light source side connection portion in which the emission end portion 31b is provided and which is provided in the second light source module 20b. The fixing portion 33b is fitted to a convex fixing portion 133b provided in the intermediary adapter 100. When the fixing portion 33b is fitted to the fixing portion 133b, the second light source module 20b is mechanically and optically connected to the intermediary adapter 100. Thus, the fixing portion 33b and the fixing portion 133b function as a second connection mechanism.

The heat radiation mechanism radiates heat generated from, for example, the second light source 21b. The heat radiation mechanism has, for example, a Peltier element and a heat radiation fin.

[Intermediary Adapter 100]

As shown in FIG. 1, the intermediary adapter 100 has a substantially cubic shape. The intermediary adapter 100 includes a first plane which is optically and mechanically connected to the first light source module 20a, a second plane which is optically and mechanically connected to the second light source module 20b and which intersects at right angles with the first plane, a third plane which is optically and mechanically connected to the first irradiation module 60a or the second irradiation module 60b and which faces the first plane and which intersects at right angles with the second plane.

As shown in FIG. 1, the intermediary adapter 100 also has a light guide member 109a which optically connects the first light source module 20a and the first irradiation module 60a to each other and which guides the first light source light from the first light source module 20a to the first irradiation module 60a, and a light guide member 109b which optically connects the second light source module 20b and the second irradiation module 60b to each other and which guides the second light source light from the second light source module 20b to the second irradiation module 60b.

The light guide member 109a has the same thickness and the same optical properties as the light guide member 29a and a later-described first light guide member 71a. The light guide member 109a is, for example, a light guide rod or a bundle fiber. It is preferable that the diameter of the light guide member 109a is, for example, several hundred μm or more.

The light guide member 109a is provided inside the intermediary adapter 100. Moreover, the light guide member 109a is linearly provided toward the third plane from the first plane. The light guide member 109a has the incidence end portion 111a which is provided on the first plane side and which is optically connected to the emission end portion 31a and which the first light source light incidences, and an emission end portion 113a which is provided on the third plane side and which is optically connected to an incidence end portion 63a of the first irradiation module 60a and from which the first light source light emissions. The incidence end portion 111a constitutes a first light guide incidence end portion of the light guide member 109a which the first light source light incidences. The incidence end portion 111a is larger than the later-described incidence end portion 111b. That is, the light guide member 109a has an incidence region larger than the light guide member 109b. The light guide member 109a guides the first light source light which has incident from the first light source module 20a via the incidence end portion 111a to the first irradiation module 60a via the emission end portion 113a.

The light guide member 109b has the same thickness and the same optical properties as the light guide member 29b and a later-described second light guide member 71b. The light guide member 109b has, for example, a single optical fiber. In this case, the optical fiber includes a core, and a cladding having a refractive index lower than the refractive index of the core. The diameter of the core is, for example, several μm to 200 μm. The light guide member 109b is covered with an unshown ferrule. It is preferable that the light guide member 109b is, for example, a multimode optical fiber.

The light guide member 109b is provided inside the intermediary adapter 100. Moreover, the light guide member 109b is provided to bend from the second plane toward the third plane. The light guide member 109b has the incidence end portion 111b which is provided on the second plane side and which is optically connected to the emission end portion 31b and which the second light source light incidences, and an emission end portion 113b which is provided on the third plane side and which is optically connected to an incidence end portion 63b of the second irradiation module 60b and from which the second light source light emissions. The incidence end portion 111b and the emission end portion 113b represent the end portions of the core. The incidence end portion 111b constitutes a second light guide incidence end portion of the light guide member 109b which the second light source light incidences. The light guide member 109b guides the second light source light which has incident from the second light source module 20b via the incidence end portion 111b to the second irradiation module 60b via the emission end portion 113b.

The intermediary adapter 100 also has the fixing portion 133a which fixes the incidence end portion 111a to the emission end portion 31a so that the emission end portion 31a and the incidence end portion 111a are optically connected to each other, and the fixing portion 133b which fixes the incidence end portion 111b to the emission end portion 31b so that the emission end portion 31b and the incidence end portion 111b are optically connected to each other.

The fixing portion 133a constitutes a first adapter side connection portion in which the incidence end portion 111a is provided and which is provided in the intermediary adapter 100 and which is mechanically connected to the fixing portion 33a so that the emission end portion 31a and the incidence end portion 111a are optically connected to each other. The fixing portion 133a is provided to stand from the first plane. The fixing portion 133a has a convex shape, and is fitted to the concave fixing portion 33a. When the fixing portion 133a is fitted to the fixing portion 33a, the intermediary adapter 100 is mechanically and optically connected to the first light source module 20a. Thus, the fixing portion 133a and the fixing portion 33a function as a first connection mechanism.

The fixing portion 133a is mechanically connected to the fixing portion 33a alone, and the incidence end portion 111a is optically connected to the emission end portion 31a alone. Therefore, the fixing portion 133a is not fitted to the fixing portion 33b, and is not mechanically connected to the fixing portion 33b (the second light source module 20b). This is achieved if, for example, the diameter of the fixing portion 133a and the diameter of the fixing portion 33b are different from each other. Accordingly, the incidence end portion 111a is not optically connected to the emission end portion 31b.

The fixing portion 133b constitutes a second adapter side connection portion in which the incidence end portion 111b is provided and which is provided in the intermediary adapter 100 and which is mechanically connected to the fixing portion 33b so that the emission end portion 31b and the incidence end portion 111b are optically connected to each other. The fixing portion 133b is provided to stand from the second plane. The fixing portion 133b has a convex shape, and is fitted to the concave fixing portion 33b. When the fixing portion 133b is fitted to the fixing portion 33b, the intermediary adapter 100 is mechanically and optically connected to the second light source module 20b. Thus, the fixing portion 133b and the fixing portion 33b function as a second connection mechanism.

The fixing portion 133b is mechanically connected to the fixing portion 33b alone, and the incidence end portion 111b is optically connected to the emission end portion 31b alone. Therefore, the fixing portion 133b is not fitted to the fixing portion 33a, and is not mechanically and optically connected to the first light source module 20a. This is achieved if, for example, the diameter of the fixing portion 133b and the diameter of the fixing portion 33a are different from each other. Accordingly, the incidence end portion 111b is not optically connected to the emission end portion 31a.

As described above, the first plane in which the fixing portion 133a is provided is different from the second plane in which the fixing portion 133b is provided, and the fixing portion 133a and the fixing portion 133b are not provided in the same plane. Thus, the position where the first light source module 20a is provided is different from the position where the second light source module 20b is provided, so that the first light source module 20a and the second light source module 20b are provided without interference with each other.

The intermediary adapter 100 also has a concave fixing portion 165 in which the emission end portion 113a is provided and which is a third adapter side connection portion provided in the intermediary adapter 100 and which is also a first adapter irradiation connection portion, and a concave fixing portion 167 in which the emission end portion 113b is provided and which is the third adapter side connection portion provided in the intermediary adapter 100 and which is also a second adapter irradiation connection portion.

The fixing portion 165 is provided to be depressed from the third plane around the emission end portion 113a. The fixing portion 165 is fitted to a fixing portion 65a provided in a first fixing unit 61a of the first irradiation module 60a, or a fixing portion 65b provided in a second fixing unit 61b of the second irradiation module 60b. When the fixing portion 165 is fitted to the fixing portion 65a, the intermediary adapter 100 is mechanically and optically connected to the first irradiation module 60a. Thus, the fixing portion 165 and the fixing portion 65a function as a third connection mechanism. While the fixing portion 165 is also fitted to the fixing portion 65b, the intermediary adapter 100 is only mechanically connected to the second irradiation module 60b and is not optically connected to the second irradiation module 60b. Thus, the fixing portion 165 and the fixing portion 65b function as the third connection mechanism.

The fixing portion 165 is not fitted to a fixing portion 67a provided in the first fixing unit 61a and a fixing portion 67b provided in the second fixing unit 61b. This is achieved if, for example, the diameter of the fixing portion 165 and the diameter of the fixing portion 67a are different from each other. The same also applies to the fixing portion 165 and the fixing portion 67b.

The fixing portion 167 is provided to be depressed from the third plane around the emission end portion 113b. The fixing portion 167 is fitted to the fixing portion 67a or the fixing portion 67b. While the fixing portion 167 is fitted to the fixing portion 67a, the intermediary adapter 100 is only mechanically connected to the second irradiation module 60b accordingly and is not optically connected to the second irradiation module 60b. Thus, the fixing portion 167 and the fixing portion 67a function as the third connection mechanism. When the fixing portion 167 is fitted to the fixing portion 67b, the intermediary adapter 100 is mechanically and optically connected to the second irradiation module 60b. Thus, the fixing portion 167 and the fixing portion 67b function as the third connection mechanism.

The fixing portion 167 is not fitted to the fixing portion 65a and the fixing portion 65b. This is achieved if, for example, the diameter of the fixing portion 167 and the diameter of the fixing portion 65a are different from each other. The same also applies to the fixing portion 167 and the fixing portion 65b.

Thus, the intermediary adapter 100 optically intervenes between the first light source module 20a and the first irradiation module 60a, and optically intervenes between the second light source module 20b and the second irradiation module 60b. The third plane of the intermediary adapter 100, where the fixing portions 165 and 167 which are the third adapter side connection portions are provided, faces the first plane.

The intermediary adapter 100 is connected to the first irradiation module 60a or the second irradiation module 60b interchangeably in the third plane.

[First Irradiation Module 60a]

The first irradiation module 60a has the first fixing unit 61a which is optically and mechanically fixed to the intermediary adapter 100, a first light guide unit 69a which is connected to the first fixing unit 61a and which guides the first light source light, and a first light conversion unit 75a which is provided at the end portion of the first light guide unit 69a and which converts the first light source light guided by the first light guide unit 69a to illumination light and then emits the illumination light.

[First Fixing Unit 61a]

The first fixing unit 61a has the incidence end portion 63a which the first light source light incidences and which is optically connected to the emission end portion 113a, the convex fixing portion 65a in which the incidence end portion 63a is provided and which is fitted to the fixing portion 165, and the convex fixing portion 67a which is provided in the same plane as the convex fixing portion 65a and which is fitted to the fixing portion 167.

The timing of the fitting of the fixing portion 65a to the fixing portion 165 is simultaneous with the timing of the fitting of the fixing portion 67a to the fixing portion 167. Therefore, the incidence end portion 63a is optically connected to the emission end portion 113a, and the first fixing unit 61a (the first irradiation module 60a) is mechanically and optically connected to the intermediary adapter 100.

The fixing portion 67a blocks the second light source light to prevent the second light source light emitted from the emission end portion 113b from emitting to the outside when the first irradiation module 60a is connected to the intermediary adapter 100. The fixing portion 67a is provided to face the emission end portion 113b. Simultaneously with the above-mentioned timing, the fixing portion 67a abuts on the emission end portion 113b, and blocks the second light source light.

The fixing portions 65a and 67a constitute a first irradiation connection portion which is provided in the first irradiation module 60a and which is mechanically connected to the fixing portions 165 and 167 so that the first irradiation module 60a and the emission end portion 113a are optically connected to each other.

[First Light Guide Unit 69a]

The first light guide unit 69a has a first light guide member 71a which guides the first light source light to the first light conversion unit 75a, and an envelope 73 which covers the first light guide member 71a.

The first light guide member 71a has one end portion which is provided in the first fixing unit 61a and which functions as the incidence end portion 63a, and the other end portion which is optically connected to the first light conversion unit 75a. The first light guide member 71a is freely bendable. This first light guide member 71a has, for example, a single optical fiber or a bundle fiber. The first light guide member 71a is provided to be, for example, linearly bendable.

The envelope 73 covers the first light guide member 71a extended from the first fixing unit 61a and exposed from the first fixing unit 61a. The envelope 73 also covers the first light conversion unit 75a.

[First Light Conversion Unit 75a]

The first light conversion unit 75a converts the optical properties of the first light source light guided by the first light guide member 71a, and converts the first light source light to desired illumination light. More specifically, the first light conversion unit 75a converts at least one of a peak wavelength, a spectrum shape, a radiation angle, and a light amount included in the optical properties of the first light source light to a desirable state. When the first light conversion unit 75a converts, for example, the light amount of the first light source light alone, the first light conversion unit 75a directly emits the first light source light.

The first light conversion unit 75a according to the present embodiment may have a radiation angle conversion member which converts the radiation angle of the first light source light to a desired radiation angle. The radiation angle conversion member is a kind of light distribution conversion member which expands the radiation angle. The radiation angle conversion member has, for example, a single concave lens or a lens group formed by a combination of lenses which converts the radiation angle to a desired radiation angle. The first light conversion unit 75a only coverts the radiation angle of the first light source light by the radiation angle conversion member so that the peak wavelength and spectrum shape of the first light source light are hardly changed. The first light conversion unit 75a emits the first light source light as illumination light by the radiation angle conversion member.

[Second Irradiation Module 60b]

The second irradiation module 60b has the second fixing unit 61b which is optically and mechanically fixed to the intermediary adapter 100, a second light guide unit 69b which is connected to the second fixing unit 61b and which guides the second light source light, and a second light conversion unit 75b which is provided at the end portion of the second light guide unit 69b and which converts the second light source light guided by the second light guide unit 69b to illumination light and then emits the illumination light.

[Second Fixing Unit 61b]

The second fixing unit 61b has the incidence end portion 63b which the second light source light incidences and which is optically connected to the emission end portion 113b, the convex fixing portion 65b which is fitted to the fixing portion 165, and the fixing portion 67b in which the incidence end portion 63b is provided and which is provided in the same plane as the convex fixing portion 65b and which is fitted to the fixing portion 167.

The timing of the fitting of the fixing portion 65b to the fixing portion 165 is simultaneous with the timing of the fitting of the fixing portion 67b to the fixing portion 167. Therefore, the incidence end portion 63b is optically connected to the emission end portion 113b, and the second fixing unit 61b (the second irradiation module 60b) is mechanically and optically connected to the intermediary adapter 100.

The fixing portion 65b blocks the first light source light to prevent the first light source light emitted from the emission end portion 113a from emitting to the outside when the second irradiation module 60b is connected to the intermediary adapter 100. The fixing portion 65b is provided to face the emission end portion 113a. Simultaneously with the above-mentioned timing, the fixing portion 65b abuts on the emission end portion 113a, and blocks the first light source light.

The fixing portions 65b and 67b constitute a second irradiation connection portion which is provided in the second irradiation module 60b and which is mechanically connected to the fixing portions 165 and 167 so that the second irradiation module 60b and the emission end portion 113b are optically connected to each other.

[Second Light Guide Unit 69b]

The second light guide unit 69b has the second light guide member 71b which guides the second light source light to the second light conversion unit 75b, and an envelope 73 which covers the second light guide member 71b.

The second light guide member 71b has one end portion which is provided in the second fixing unit 61b and which functions as the incidence end portion 63b, and the other end portion which is optically connected to the second light conversion unit 75b. The second light guide member 71b is freely bendable. This second light guide member 71b has, for example, a single optical fiber. The second light guide member 71b is provided to be, for example, linearly bendable.

The envelope 73 covers the second light guide member 71b extends from the second fixing unit 61b and exposed from the second fixing unit 61b. The envelope 73 also covers the second light conversion unit 75b.

[Second Light Conversion Unit 75b]

The second light conversion unit 75b converts the optical properties of the second light source light guided by the second light guide member 71b, and converts the second light source light to desired illumination light. More specifically, the light conversion unit has a spectrum conversion member which absorbs some of the second light source light (blue laser light), converts the light to yellow fluorescence, and emits the yellow fluorescence, which absorbs the rest of the second light source light (blue laser light), converts the light to blue scattered light, and emits the blue scattered light. The spectrum conversion member is, for example, a wavelength conversion member which converts at least one of a peak wavelength, a spectrum shape, a radiation angle, and a light amount included in the optical properties of the second light source light to a desirable state. In this case, the spectrum conversion member is formed by, for example, the dispersion of YAG:Ce fluorescence powder on a resin or glass.

The yellow fluorescence and the scattered light are mixed with each other, and emitted as mixed light. In this instance, the ratio between the light amount of the yellow fluorescence and the light amount of the scattered light can be adjusted by the thickness and shape of the spectrum conversion member and the particle diameter and concentration of the fluorescence powder. The color of the mixed light can be adjusted by the ratio between the light amount of the yellow fluorescence and the light amount of the scattered light. In the present embodiment, the ratio between the light amount of the yellow fluorescence and the light amount of the scattered light is adjusted by the thickness and shape of the spectrum conversion member and the particle diameter and concentration of the fluorescence powder so that the mixed light will be white light.

[Function 1]

The first light source module 20a is connected to the intermediary adapter 100, and the first irradiation module 60a is connected to the intermediary adapter 100. The first light source module 20a is connected to an unshown light source driving unit which controls the first light source module 20a.

The fixing portion 33a is fitted to the fixing portion 133a so that the emission end portion 31a and the incidence end portion 111a are optically connected to each other. The fixing portions 65a and 67a are fitted to the fixing portions 165 and 167 so that the emission end portion 113a and the incidence end portion 63a are optically connected to each other.

The first light source 21a emits the first light source light. The first light source light travels through the emission end portion 31a, the incidence end portion 111a, the light guide member 109a, the emission end portion 113a, the incidence end portion 63a, the first light guide member 71a, and the first light conversion unit 75a in order. The first light source light is emitted to the outside from the first light conversion unit 75a so that the radiation angle thereof is expanded by the first light conversion unit 75a. The first light source light then illuminates an observation target as illumination light.

The first light source light which is lamp light is white light having a spectrum relatively close to that of sunlight. Thus, the combination of the first light source module 20a and the first irradiation module 60a is advantageous to the application of light approximate to sunlight to an illumination target.

[Function 2]

The second light source module 20b is connected to the intermediary adapter 100, and the second irradiation module 60b is connected to the intermediary adapter 100. The second light source module 20b is connected to an unshown light source driving unit which controls the second light source module 20b.

The light source driving unit may be either combined with or separate from the light source driving unit which controls the first light source module 20a.

The fixing portion 33b is fitted to the fixing portion 133b so that the emission end portion 31b and the incidence end portion 111b are optically connected to each other. The fixing portions 65b and 67b are fitted to the fixing portions 165 and 167 so that the emission end portion 113b and the incidence end portion 63b are optically connected to each other.

The second light source 21b emits the second light source light. The second light source light travels through the emission end portion 31b, the incidence end portion 111b, the light guide member 109b, the emission end portion 113b, the incidence end portion 63b, the second light guide member 71b, and the second light conversion unit 75b in order. Some of the second light source light which is blue laser light is absorbed by the spectrum conversion member of the second light conversion unit 75b, and converted to yellow fluorescence by the spectrum conversion member. The rest of the blue second light source light is converted to blue scattered light by the spectrum conversion member. The yellow fluorescence and the blue scattered light are emitted to the outside from the spectrum conversion member. In this case, the yellow fluorescence and the blue scattered light are mixed and then emitted as white light. The white light illuminates an illumination target as illumination light.

The second light source 21b having the semiconductor laser can be smaller in size and lower in electric power consumption than the first light source 21a having the lamp light source or the LED light source. Therefore, if the second light source module 20b and the second irradiation module 60b are combined, the light source system 10 is reduced in size and applies the illumination light with low electric power consumption. The laser light is brighter than the lamp light or the LED light. Thus, the combination of the second light source module 20b and the second irradiation module 60b is advantageous when the light source system 10 is needed to be reduced in size, when the electric power of the light source system 10 is limited, or when efficient and bright white light is needed.

Advantageous Effects

Thus, according to the present embodiment, the intermediary adapter 100 optically intervenes between the first light source module 20a and the first irradiation module 60a, and optically intervenes between the second light source module 20b and the second irradiation module 60b. The irradiation modules 60a and 60b are optically connected to the light source modules 20a and 20b. One of the first irradiation module 60a and the second irradiation module 60b is provided in the third plane. Consequently, according to the present embodiment, the plane to which the irradiation modules 60a and 60b are connected is located in the same third plane regardless of the kinds of the irradiation modules 60a and 60b, so that the trouble of the assembly can be saved, accurate and easy assembly is possible, and various types of illumination light suited to the purpose can be emitted.

For example, when the first light source module 20a and the second light source module 20b are previously connected to the intermediary adapter 100 and when the first irradiation module 60a is connected to the intermediary adapter 100, light close to sunlight can be applied to the irradiation target by the operation of the first light source module 20a. When the intermediary adapter 100 is connected to the second irradiation module 60b, brighter light can be applied to the irradiation target by the operation of the second light source module 20b.

In each case, illumination light suited to the function and property can be emitted in accordance with the kind of irradiation module connected to the intermediary adapter 100, and the burden on the user can be reduced.

According to the present embodiment, in the first light source 21a, the light emitting region of the lamp light and the light emitting region of the LED light are relatively large, and the optical properties of the lamp light and the optical properties of the LED light are approximately equal to each other. Thus, even when the first light source 21a emits the LED light, the LED light can be guided if a bundle fiber is used for the light guide member 109a. A light source which emits the lamp light and light source which emits the LED light may be prepared as the first light source module 20a, and may be interchangeable. Light sources having different emission spectrums of LED light may be prepared, and may be interchangeable.

According to the present embodiment, the first light conversion unit 75a hardly changes the peak wavelengths and the spectrum shapes of the lamp light and the LED light, and only converts their radiation angles and then applies the lamp light and the LED light to the illumination target. Therefore, according to the present embodiment, the first light conversion unit 75a can also be shared by the lamp light and the LED light.

According to the present embodiment, for example, in the combination of the second light source module 20b and the second irradiation module 60b, the operation of the second light conversion unit 75b varies according to the wavelength of the laser light.

For example, in the second light conversion unit 75b, the spectrum conversion member having the above-mentioned YAG:Ce fluorescence powder absorbs the blue laser light, and converts the blue laser light to yellow fluorescence. In this instance, the spectrum conversion member does not absorb and convert blue-violet laser light and laser light longer in wavelength than green.

However, the spectrum conversion member according to the present embodiment also functions as a radiation angle conversion member which converts the radiation angle of the laser light regardless of the wavelength of the laser light. Therefore, the spectrum conversion member converts the wavelength of the blue laser light, and emits white illumination light so that the radiation angle of the illumination light is converted. The spectrum conversion member also emits blue-violet laser light and laser light longer in wavelength than green so that their radiation angles are converted.

As described above, because of the intervention of the intermediary adapter 100, more than one kind of irradiation module can be interchangeably connected and operated, and various types of illumination light suited to the purpose can be emitted.

According to the present embodiment, the first light conversion unit 75a has the radiation angle conversion member (a kind of light distribution conversion member), and the second light conversion unit 75b has the spectrum conversion member. However, the present invention does not need to be limited to this. One example is described below. It should be appreciated that matters described below may be used in combination, or may be independently used.

A: For example, the first light conversion unit 75a may have at least one of a concave lens, a convex lens, a hologram lens, and a diffraction grating. The concave lens, the convex lens, and a combination of the concave lens and the convex lens function as the radiation angle conversion member which converts the radiation angle of the illumination light. The hologram lens and the diffraction grating function as the radiation angle conversion member, or as a radiation conversion member which converts the radiation direction of the illumination light.

B: For example, in the first light conversion unit 75a, the radiation conversion member may be made of a resin or glass in which particles are dispersed. The particles are, for example, alumina having a high refractive index and a high reflectivity. Alternatively, for example, the radiation conversion member may be made of transparent members different in refractive index. Alternatively, for example, the radiation conversion member may be formed by a scattering plate such as frosted glass, or by a diffusion plate having minute depressions and projections provided in its surface.

C: In the second light conversion unit 75b, the spectrum conversion member may have at least one of an optical semiconductor material, an SHG (secondary harmonic) material, and an electroluminescent material.

D, E: The second light conversion unit 75b may be formed by a member which transmits some of the light source light and blocks the rest of the light source light.

D: This member is, for example, an optical filter. This optical filter represents, for example, at least one of a wavelength cut filter, a dye filter, and an optical resonator (etalon).

E: This member is, for example, a light transmitting modulation member. The light transmitting modulation member represents, for example, at least one of an optical switch, an electrochromic element, and a liquid crystal device.

For example, B is suited to the safety of the second light source 21b and speckle removal. When the radiation angles of the lamp light and the LED light are adjusted in the first light source 21a, at least one of A and B can be used.

[First Modification]

Now, a first modification of the present embodiment is described with reference to FIG. 2A.

Figure 2A:
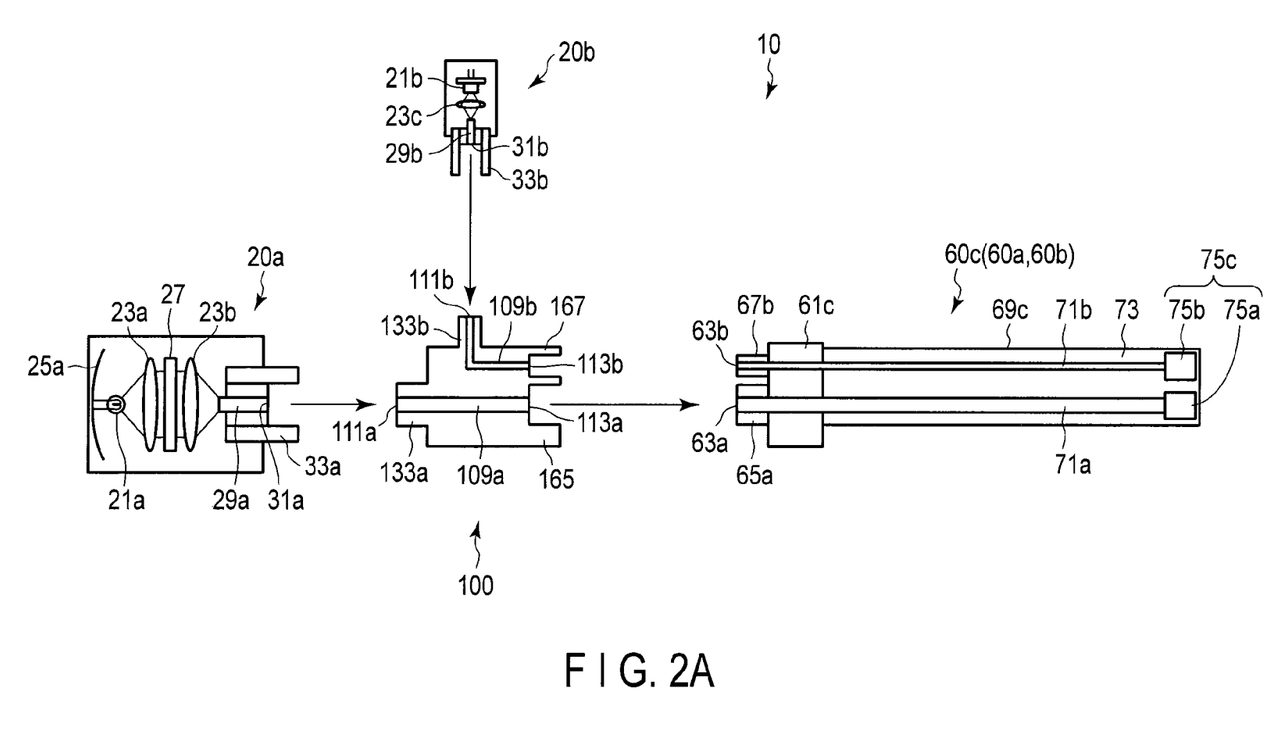
FIG. 2A is a schematic diagram of the light source system according to a first modification of the first embodiment.

As shown in FIG. 2A, the light source system 10 has a third irradiation module 60c formed by a combination of the first irradiation module 60a and the second irradiation module 60b.

Thus, the third irradiation module 60c functions by receiving at least one of the first light source light and the second light source light.

The third irradiation module 60c has a third fixing unit 61c which is optically and mechanically fixed to the intermediary adapter 100, a third light guide unit 69c which is connected to the third fixing unit 61c and which guides at least one of the first light source light and the second light source light, and a third light conversion unit 75c which is provided at the end portion of the third light guide unit 69c and which converts at least one of the first light source light and the second light source light guided by the third light guide unit 69c to illumination light and then emits the illumination light.

[Third Fixing Unit 61c]

The third fixing unit 61c has a substantially rectangular-parallelepiped shape. The third fixing unit 61c has the incidence end portion 63a, the incidence end portion 63b, the fixing portion 65a, and the fixing portion 67b.

[Third Light Guide Unit 69c]

The third light guide unit 69c has the first light guide member 71a, the second light guide member 71b, and an envelope 73 which covers the first light guide member 71a and the second light guide member 71b.

The first light guide member 71a and the second light guide member 71b are provided parallel to each other and linearly.

[Third Light Conversion Unit 75c]

The third light conversion unit 75c has the first light conversion unit 75a and the second light conversion unit 75b. The first light conversion unit 75a is optically connected to the first light guide member 71a alone. The second light conversion unit 75b is optically connected to the second light guide member 71b alone. The first light conversion unit 75a and the second light conversion unit 75b are optically independent of each other, and are provided apart from each other. The first light conversion unit 75a and the second light conversion unit 75b are provided flush in a plane which intersects at right angles with the axial direction of the light guide unit.

The first light source light (the lamp light and the LED light) has optical properties similar to the optical properties of the second light source light (the blue laser light). That is, the first light source light has a blue component which is absorbed by the spectrum conversion member of the second light conversion unit 75b and which is converted to yellow fluorescence by the spectrum conversion member. Therefore, if the second light conversion unit 75b is optically connected to the first light guide member 71a, illumination light including the yellow fluorescence is radiated even when the first light source light is applied to the second light conversion unit 75b. To avoid this, the second light conversion unit 75b is optically independent of the first light guide member 71a. Thus, the first light source light is not applied to the second light conversion unit 75b, and the second light source light is not applied to the first light conversion unit 75a.

According to the present modification, the intermediary adapter 100 is used together with the third irradiation module 60c equipped with both the first light conversion unit 75a which uses the first light source light and the second light conversion unit 75b which uses the second light source light, so that the trouble of the assembly can be further saved.

[Second Modification]

Now, a second modification of the present embodiment is described with reference to FIG. 2B and FIG. 2C.

Figure 2B:
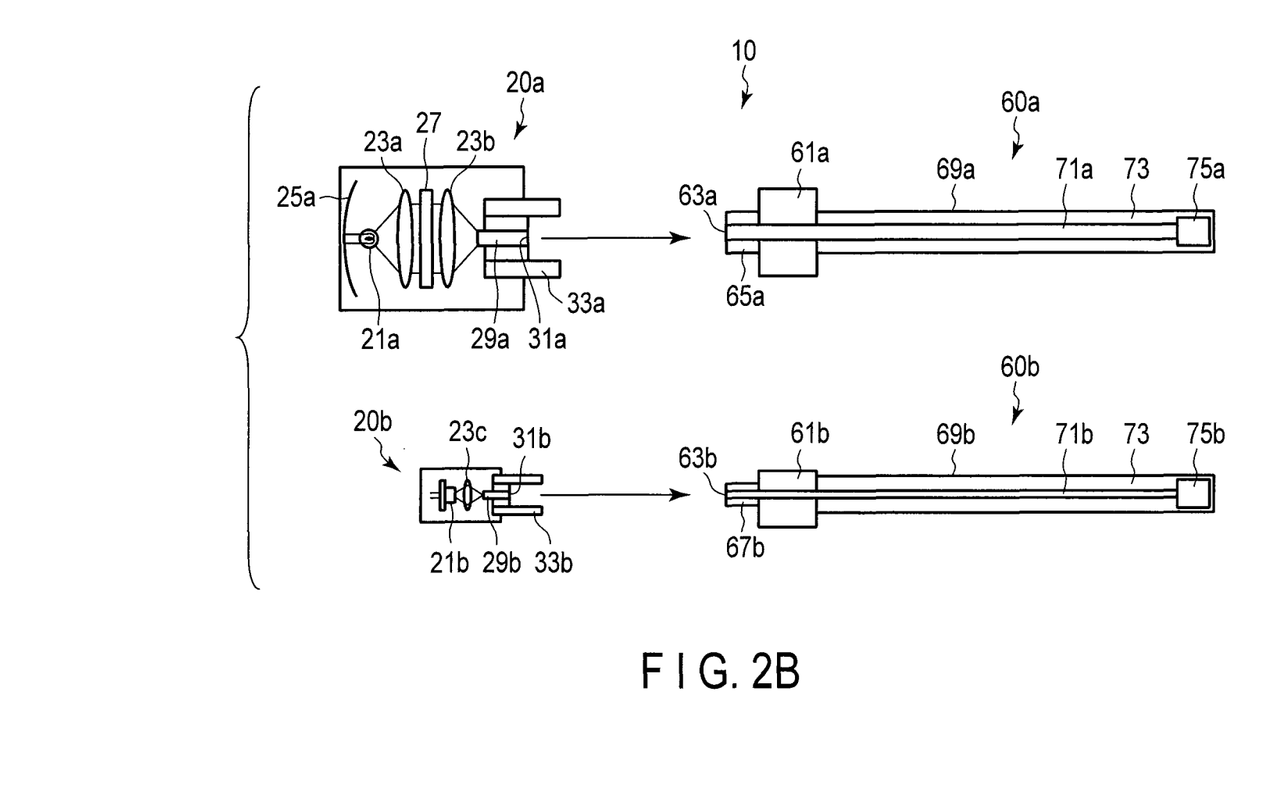
FIG. 2B is a schematic diagram of the light source system according to a second modification of the first embodiment.

According to the present modification, as shown in FIG. 2B, the first light source module 20a may be optically and mechanically connected directly to the first irradiation module 60a. In this case, the first fixing unit 61a only has the incidence end portion 63a and the fixing portion 65a. The fixing portion 65a is directly fitted to the fixing portion 33a so that the emission end portion 31a and the incidence end portion 63a are optically connected to each other.

According to the present modification, as shown in FIG. 2B, the second light source module 20b may be optically and mechanically connected directly to the second irradiation module 60b. In this case, the second fixing unit 61b only has the incidence end portion 63b and the fixing portion 67b. The fixing portion 67b is directly fitted to the fixing portion 33b so that the emission end portion 31b and the incidence end portion 63b are optically connected to each other.

Thus, the fitting of the fixing portion 65a and the fixing portion 33a is performed separately from the fitting of the fixing portion 67b and the fixing portion 33b.

Figure 2C:
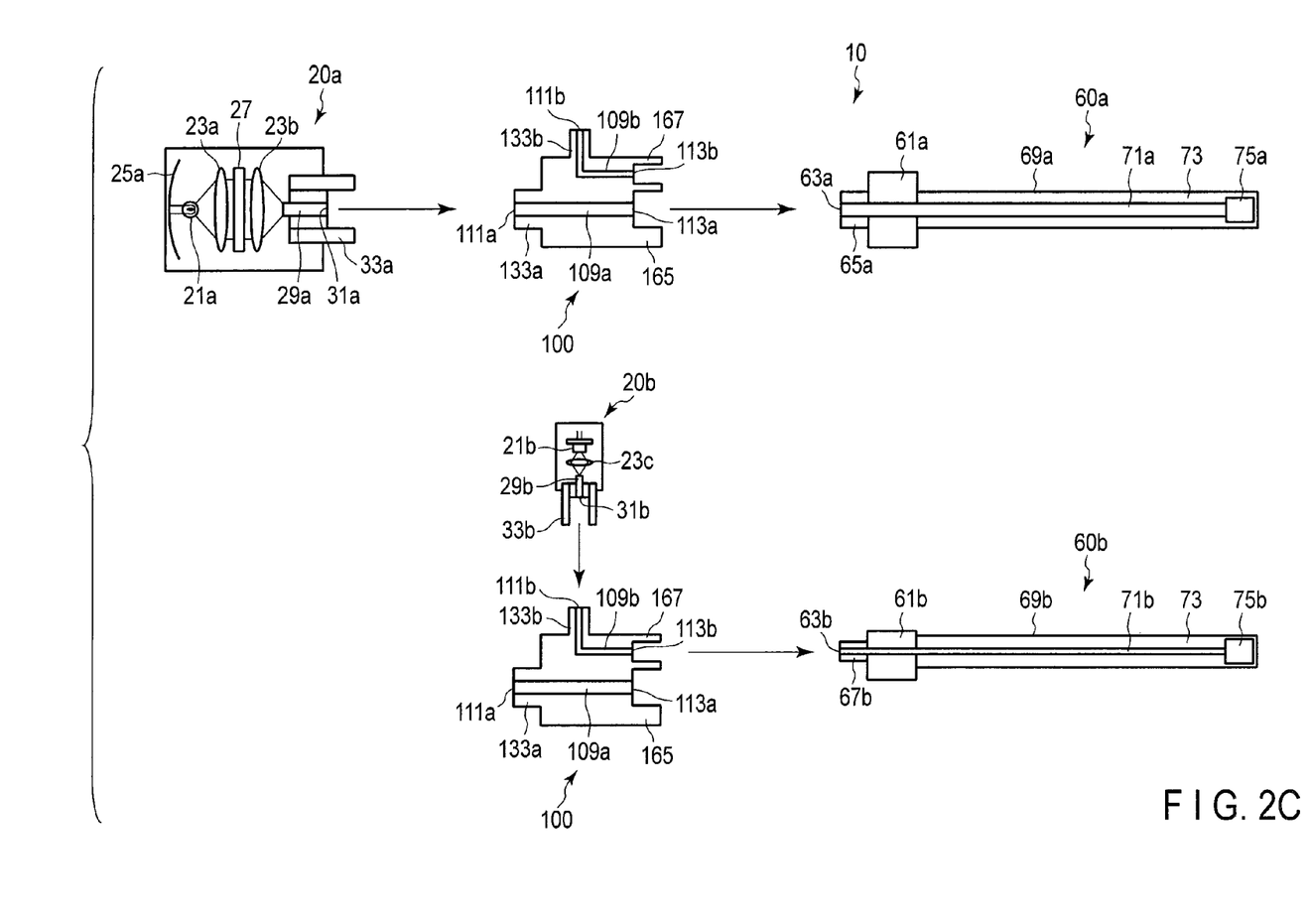
FIG. 2C is a schematic diagram of the light source system according to the second modification of the first embodiment.

As shown in FIG. 2C, when the intermediary adapter 100 is provided, the fixing portion 65a has only to be fitted to the fixing portion 165 so that the emission end portion 113a and the incidence end portion 63a are optically connected to each other. Moreover, as shown in FIG. 2C, the fixing portion 67b has only to be fitted to the fixing portion 167 so that the emission end portion 113b and the incidence end portion 63b are optically connected to each other.

Thus, the fitting (mechanical connection) of the fixing portion 65a and the fixing portion 165 and the fitting (mechanical connection) of the fixing portion 67b and the fixing portion 167 are separately and independently performed.

According to the present modification, the irradiation module which is directly connected to the light source module and which is operable is connected to the light source module via the intermediary adapter 100, so that more than one kind of irradiation module can be connected in the same plane of the intermediary adapter 100, and the assembly can be simpler.

Second Embodiment

A second embodiment is described with reference to FIG. 3A and FIG. 3B. In the present embodiment, components different from the components according to the first embodiment are only described below.

[Configuration]

Figure 3A:
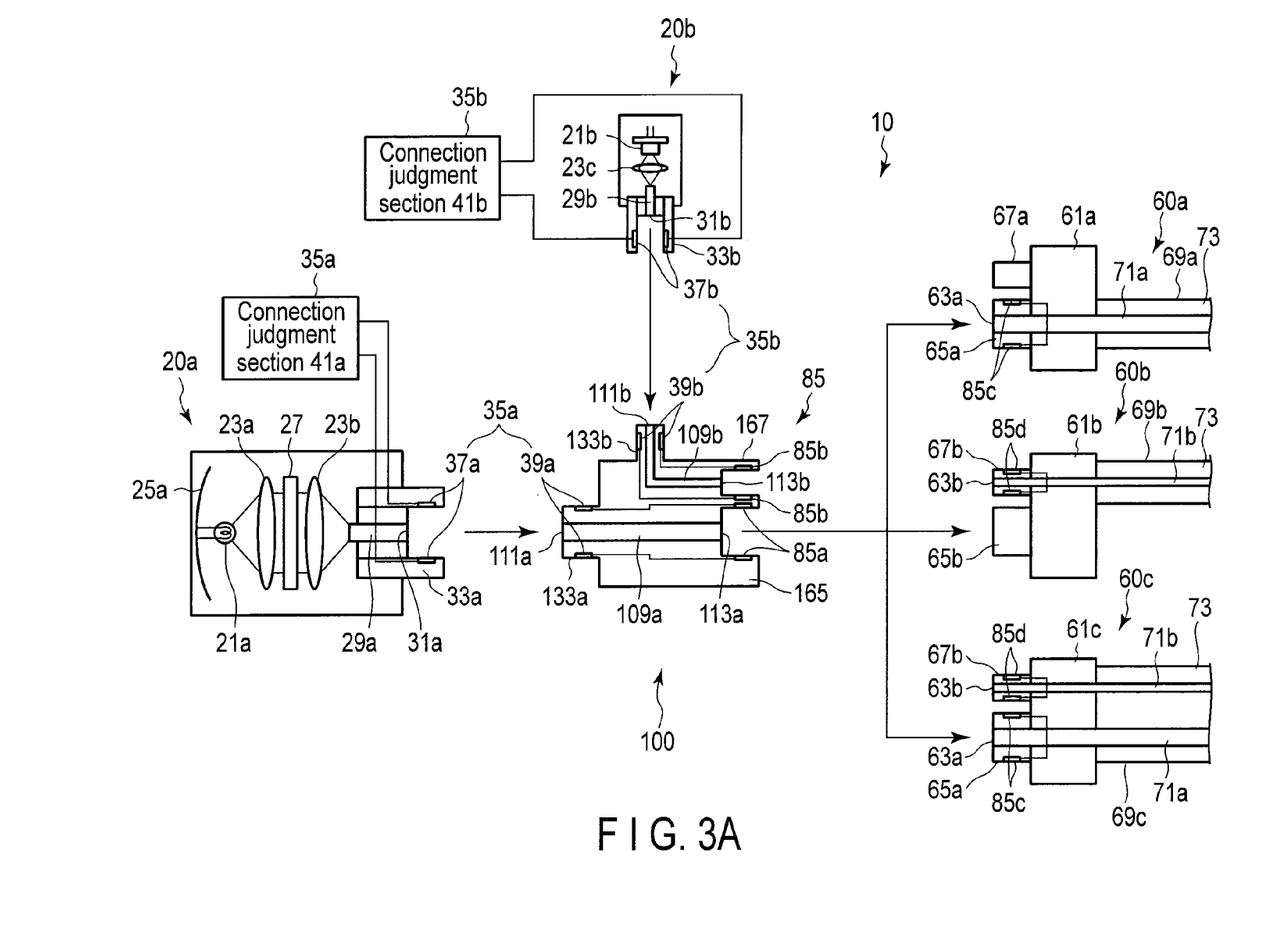
FIG. 3A is a schematic diagram of a light source system according to a second embodiment.

As shown in FIG. 3A, the first connection mechanism further has a detecting portion 35a which detects the connection of the fixing portion 33a and the fixing portion 133a. The detecting portion 35a has a pair of electrodes 37a provided in the fixing portion 33a, a pair of electrodes 39a provided in the fixing portion 133a, and a connection judgment section 41a electrically connected to the electrodes 37a.

When the fixing portion 33a and the fixing portion 133a are connected to each other, the electrodes 37a and the electrodes 39a are electrically connected to each other. The connection judgment section 41a judges the conduction between the electrodes 37a and the electrodes 39a. On the basis of this judgment result, the connection judgment section 41a judges the connection of the fixing portion 33a and the fixing portion 133a, that is, the optical connection of the emission end portion 31a and the incidence end portion 111a. The connection judgment section 41a is connected to the unshown light source driving unit, and transmits the judgment result by the connection judgment section 41a to the light source driving unit.

When the judgment result shows that the fixing portion 33a and the fixing portion 133a are connected to each other, the light source driving unit drives the first light source module 20a. When the judgment result shows that the fixing portion 33a and the fixing portion 133a are not connected to each other, the light source driving unit stops the first light source module 20a.

The second connection mechanism further has a detecting portion 35b which detects the connection of the fixing portion 33b and the fixing portion 133b. The detecting portion 35b has a pair of electrodes 37b provided in the fixing portion 33b, a pair of electrodes 39b provided in the fixing portion 133b, and a connection judgment section 41b electrically connected to the electrodes 37b.

When the fixing portion 33b and the fixing portion 133b are connected to each other, the electrodes 37b and the electrodes 39b are electrically connected to each other. The connection judgment section 41b judges the conduction between the electrodes 37b and the electrodes 39b. On the basis of this judgment result, the connection judgment section 41b judges the connection of the fixing portion 33b and the fixing portion 133b, that is, the optical connection of the emission end portion 31b and the incidence end portion 111b. The connection judgment section 41b is connected to the unshown light source driving unit, and transmits the judgment result by the connection judgment section 41b to the light source driving unit.

When the judgment result shows that the fixing portion 33b and the fixing portion 133b are connected to each other, the light source driving unit drives the second light source module 20b. When the judgment result shows that the fixing portion 33b and the fixing portion 133b are not connected to each other, the light source driving unit stops the second light source module 20b.

The third connection mechanism further has a detecting portion 85 which detects the connection of the fixing portion 165 and the fixing portion 65a and the connection of the fixing portion 167 and the fixing portion 67b. The detecting portion 85 has a pair of electrodes 85a provided in the fixing portion 165, a pair of electrodes 85b provided in the fixing portion 167, a pair of electrodes 85c provided in the fixing portion 65a, and a pair of electrodes 85d provided in the fixing portion 67b.

The electrodes 85c are provided to correspond to the electrodes 85a and the first light guide member 71a. That is, the electrodes 85c are provided for the first light source module 20a.

The electrodes 85d are provided to correspond to the electrodes 85b and the second light guide member 71b. That is, the electrodes 85d are provided for the second light source module 20b.

The electrodes 85a are electrically connected to the electrodes 39a. When the fixing portion 165 and the fixing portion 65a are connected to each other, the electrodes 85a and the electrodes 85c are electrically connected to each other.

The electrodes 85b are electrically connected to the electrodes 39b. When the fixing portion 167 and the fixing portion 67b are connected to each other, the electrodes 85b and the electrodes 85d are electrically connected to each other.

Thus, the detecting portion 85 transmits the detection result of the connection of the fixing portion 165 and the fixing portion 65a to the detecting portion 35a, and transmits the detection result of the connection of the fixing portion 167 and the fixing portion 67b to the detecting portion 35b.

That is, when the detecting portion 35a has detected the connection of the fixing portion 33a and the fixing portion 133a and when the detecting portion 85 has detected the connection of the fixing portion 165 and the fixing portion 65a, the detecting portion 85 transmits the detection result by the detecting portion 85 to the detecting portion 35a. When the detecting portion 35b has detected the connection of the fixing portion 33b and the fixing portion 133b and when the detecting portion 85 has detected the connection of the fixing portion 167 and the fixing portion 67b, the detecting portion 85 transmits the detection result by the detecting portion 85 to the detecting portion 35b.

Figure 3B:
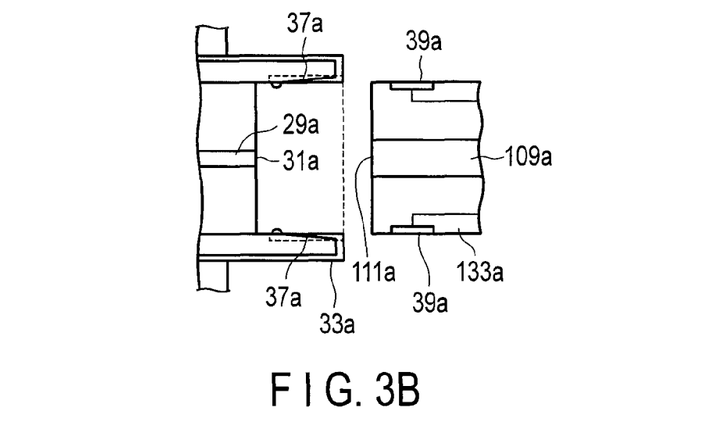
FIG. 3B is an enlarged view of a detecting portion.

As shown in FIG. 3B, the electrodes 37a are, for example, of a switch type, and are configured to contact the electrodes 39a when the fixing portion 33a contacts the fixing portion 133a. The same also applies to the electrodes 37b and the electrodes 39b, the electrodes 85a and the electrodes 85c, and the electrodes 85b and the electrodes 85d.

[Function 1]

The first light source module 20a is connected to the intermediary adapter 100, and the first irradiation module 60a is connected to the intermediary adapter 100. As a result, the fixing portion 33a and the fixing portion 133a are connected to each other, and the fixing portion 165 and the fixing portion 65a are connected to each other. Then the electrodes 37a and the electrodes 39a are connected to each other, and the electrodes 85a and the electrodes 85c are connected to each other.

The connection judgment section 41a judges the conduction between the electrodes 37a and the electrodes 39a and the conduction between the electrodes 85a and the electrodes 85c. The connection judgment section 41a judges the conduction between the electrodes 85a and the electrodes 85c via the electrodes 37a and the electrodes 39a. The connection judgment section 41a then judges that the fixing portion 33a and the fixing portion 133a are connected to each other and that the fixing portion 165 and the fixing portion 65a are connected to each other. The light source driving unit then drives the first light source module 20a. The first light source module 20a thereby controls the first light source 21a on the basis of the detection result by the detecting portion 35a and the detection result by the detecting portion 85. The first irradiation module 60a is then controlled on the basis of the detection result by the detecting portion 35a and the detection result by the detecting portion 85. The first light source 21a then emits the first light source light.

If the first irradiation module 60a is disconnected from the intermediary adapter 100, the connection judgment section 41a judges the conduction between the electrodes 85a and the electrodes 85c, and judges that the fixing portion 165 and the fixing portion 65a are disconnected from each other. The light source driving unit stops the first light source module 20a.

In Function 1, suppose that the second light source module 20b is connected to the intermediary adapter 100, the fixing portion 33b is connected to the fixing portion 133b, the electrodes 37b are connected to the electrodes 39b, and the fixing portion 167 is connected to the fixing portion 67a of the first irradiation module 60a. In this case, the first irradiation module 60a does not have the electrodes 85d, and the electrodes 85b are not connected to the electrodes 85d. Therefore, the connection judgment section 41b judges the non-conduction between the electrodes 85b and the electrodes 85d. As a result, the second light source module 20b remains stopped, and the second light source 21b does not emit the second light source light.

Thus, in Function 1, the electrodes 85c corresponding to the first light guide member 71a are provided, so that the first light source module 20a corresponding to the first light guide member 71a alone is activated, and the second light source module 20b which does not correspond to the first light guide member 71a remains stopped. Accordingly, the first light source 21a emits the first light source light, and the second light source 21b does not emit the second light source light.

[Function 2]

The second light source module 20b is connected to the intermediary adapter 100, and the second irradiation module 60b is connected to the intermediary adapter 100. As a result, the fixing portion 33b and the fixing portion 133b are connected to each other, and the fixing portion 167 and the fixing portion 67b are connected to each other. Then the electrodes 37b and the electrodes 39b are connected to each other, and the electrodes 85b and the electrodes 85d are connected to each other.

The connection judgment section 41b judges the conduction between the electrodes 37b and the electrodes 39b, and the conduction between the electrodes 85b and the electrodes 85d. The connection judgment section 41b judges the conduction between the electrodes 85b and the electrodes 85d via the electrodes 37b and the electrodes 39b. The connection judgment section 41b thereby judges that the fixing portion 33b and the fixing portion 133b are connected to each other and that the fixing portion 167 and the fixing portion 67b are connected to each other. The light source driving unit then drives the second light source module 20b. The second light source module 20b thereby controls the second light source 21b on the basis of the detection result by the detecting portion 35b and the detection result by the detecting portion 85. The second irradiation module 60b is then controlled on the basis of the detection result by the detecting portion 35b and the detection result by the detecting portion 85. The second light source 21b then emits the second light source light.

If the second irradiation module 60b is disconnected from the intermediary adapter 100, the connection judgment section 41b judges the conduction between the electrodes 85b and the electrodes 85d, and judges that the fixing portion

167 and the fixing portion 67*b* are disconnected from each other. The light source driving unit stops the second light source module 20*b*.

In Function 2, suppose that the first light source module 20*a* is connected to the intermediary adapter 100, the fixing portion 33*a* is connected to the fixing portion 133*a*, the electrodes 37*a* are connected to the electrodes 39*a*, and the fixing portion 165 is connected to the fixing portion 65*b* of the second irradiation module 60*b*. In this case, the second irradiation module 60*b* does not have the electrodes 85*c*, and the electrodes 85*a* are not connected to the electrodes 85*c*.

Therefore, the connection judgment section 41*a* judges the non-conduction between the electrodes 85*b* and the electrodes 85*c*. As a result, the first light source module 20*a* remains stopped, and the first light source 21*a* does not emit the first light source light.

Thus, in Function 2, the electrodes 85*d* corresponding to the second light guide member 71*b* are provided, so that the second light source module 20*b* corresponding to the second light guide member 71*b* alone is activated, and the first light source module 20*a* which does not correspond to the second light guide member 71*b* remains stopped. Accordingly, the second light source 21*b* emits the second light source light, and the first light source 21*a* does not emit the first light source light.

[Function 3]

The first light source module 20*a* and the second light source module 20*b* are connected to the intermediary adapter 100, and the third irradiation module 60*c* is connected to the intermediary adapter 100. As a result, Function 1 and Function 2 are combined, and the light source driving unit drives the first light source module 20*a* and the second light source module 20*b*.

That is, in Function 3, the electrodes 85*c* corresponding to the first light guide member 71*a* are provided, and the electrodes 85*d* corresponding to the second light guide member 71*b* are provided, so that both the first light source module 20*a* corresponding to the first light guide member 71*a* and the second light source module 20*b* corresponding to the second light guide member 71*b* are activated. Accordingly, the first light source 21*a* emits the first light source light, and the second light source 21*b* emits the second light source light.

If the third irradiation module 60*c* is disconnected from the intermediary adapter 100, the light source driving unit stops the first light source module 20*a* and the second light source module 20*b* in the same manner as above.

Advantageous Effects

According to the present embodiment, the connection of the light source module and the irradiation module can be detected by the detecting portions 35*a*, 35*b*, and 85. Thus, according to the present embodiment, it is possible to ensure that the light source module is operated, ensure that an unnecessary light source module is stopped, prevent unnecessary light from leaking out of the light source system 10, and increase the efficiency of light use.

According to the present embodiment, for example, in Function 1, the first light source module 20*a* controls the first light source 21*a* on the basis of the detection result by the detecting portion 35*a* and the detection result by the detecting portion 85 so that the first light source 21*a* quickly emits the first light source light. However, the present invention does not need to be limited to this. For example, the first light source module 20*a* may control the first light source 21*a* on the basis of the detection result by the detecting portion 35*a* and the detection result by the detecting portion 85 so that the first light source 21*a* is ready to emit the first light source light. That is, the first light source 21*a* is ready to be able to be driven so that the first light source 21*a* emits the first light source light in accordance with user permission. In this case, the user operates, for example, an unshown switch provided in the first light source module 20*a* to permit the driving of the first light source 21*a*.

The same also applies to the second light source 21*b* in Function 2, and at least one of the first light source 21*a* and the second light source 21*b* in Function 3.

Third Embodiment

In the present embodiment, only components that are different from the components according to the first embodiment are described below.

Figure 4:
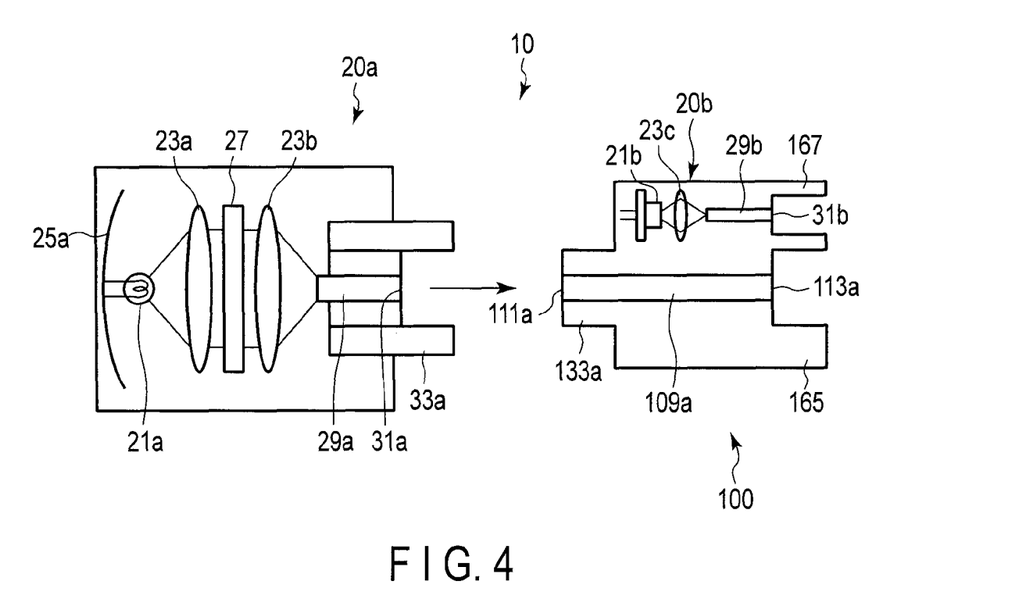
FIG. 4 is a schematic diagram of a second light source module and an intermediary adapter of a light source system according to a third embodiment.

As shown in FIG. 4, the second light source module 20*b* is incorporated in the intermediary adapter 100. Thus, according to the present embodiment, the light source system 10 can be reduced in size.

The present invention is not completely limited to the embodiments described above, and modifications of components can be made at the stage of carrying out the invention without departing from the spirit thereof. Various inventions can be made by properly combining the components disclosed in the embodiments described above.

What is claimed is:

1. An intermediary adapter comprising:
   a first adapter side connection portion which is mechanically connected to a first light source side connection portion that is provided in a first light source module that emits first light source light;
   a second adapter side connection portion which is mechanically connected to a second light source side connection portion that is provided in a second light source module that emits second light source light;
   a first light guide member which guides the first light source light; and
   a second light guide member which guides the second light source light, wherein
   the first light source module and a first irradiation module which functions by receiving the first light source light that is guided by the first light guide member or a third irradiation module which functions by receiving the first light source light that is guided by the first light guide member are optically connected by the first light guide member,
   the second light source module and a second irradiation module which functions by receiving the second light source light that is guided by the second light guide member or the third irradiation module which functions by receiving the second light source light that is guided by the second light guide member are optically connected by the second light guide member, and
   the first irradiation module, the second irradiation module and the third irradiation module is each mechanically attachable to and detachable from the intermediary adapter and each mechanically and interchangeably connected to the intermediary adapter in a same plane of the intermediary adapter.

2. The intermediary adapter according to claim 1, wherein
   a first light guide incidence end portion of the first light guide member is provided in the first adapter side connection portion, the first light source light which is emitted from a first light source emission end portion provided in the first light source side connection portion incident upon the first light guide incidence end portion, the first adapter side connection portion is mechanically connected to the first light source side connection portion so that the first light source emission end portion and the first light guide incidence end portion are optically connected, a second light guide incidence end portion of the second light guide member is provided in the second adapter side connection portion, the second light source light which is emitted from a second light source emission end portion provided in the second light source side connection portion incident upon the second light guide incidence end portion, the second adapter side connection portion is mechanically connected to the second light source side connection portion so that the second light source emission end portion and the second light guide incidence end portion are optically connected.

3. The intermediary adapter according to claim 2, further comprising;

a third adapter side connection portion which comprises a first light guide emission end portion of the first light guide member from which the first light source light is emitted, and a second light guide emission end portion of the second light guide member from which the second light source light is emitted, the third adapter side connection portion being mechanically connected to at least one of the first irradiation module, the second irradiation module, and the third irradiation module, wherein the third adapter side connection portion is mechanically connected to a first irradiation connection portion which is provided in the first irradiation module or the third irradiation module so that the first irradiation module or the third irradiation module and the first light guide emission end portion are optically connected, and the third adapter side connection portion is mechanically connected to a second irradiation connection portion which is provided in the second irradiation module or the third irradiation module so that the second irradiation module or the third irradiation module and the second light guide emission end portion are optically connected.

4. The intermediary adapter according to claim 3, wherein the first adapter side connection portion is mechanically connected only to the first light source side connection portion, the second adapter side connection portion is mechanically connected only to the second light source side connection portion.

5. The intermediary adapter according to claim 3, wherein the first light guide incidence end portion is optically connected only to the first light source emission end portion, the second light guide incidence end portion is optically connected only to the second light source emission end portion.

6. The intermediary adapter according to claim 3, wherein a first plane of the intermediary adapter where the first adapter side connection portion is provided is different from a second plane of the intermediary adapter where the second adapter side connection portion is provided.

7. The intermediary adapter according to claim 3, wherein a first plane of the intermediary adapter in which the first adapter side connection portion is provided faces a third plane of the intermediary adapter in which the third adapter side connection portion is provided, and the first light guide member is linearly provided toward the third plane from the first plane.

8. The intermediary adapter according to claim 3, wherein the first adapter side connection portion comprises a first electrode included in a first detecting portion which detects the connection of the first light source side connection portion and the first adapter side connection portion, the second adapter side connection portion comprises a second electrode included in a second detecting portion which detects the connection of the second light source side connection portion and the second adapter side connection portion, the third adapter side connection portion comprises third and fourth electrodes included in a third detecting portion which detects the connection of the third adapter side connection portion and the first irradiation connection portion and detects the connection of the third adapter side connection portion and the second irradiation connection portion, and the third detecting portion transmits a detection result by the third detecting portion to the first detecting portion and the second detecting portion.

9. The intermediary adapter according to claim 8, wherein when the first detecting portion has detected the connection of the first light source side connection portion and the first adapter side connection portion and when the third detecting portion has detected the connection of the third adapter side connection portion and the first irradiation connection portion, the third detecting portion transmits the detection result by the third detecting portion to the first detecting portion, and when the second detecting portion has detected the connection of the second light source side connection portion and the second adapter side connection portion and when the third detecting portion has detected the connection of the third adapter side connection portion and the second irradiation connection portion, the third detecting portion transmits the detection result by the third detecting portion to the second detecting portion.

10. The intermediary adapter according to claim 8, wherein the first detecting portion detects the optical connection of the first light source emission end portion and the first light guide incidence end portion, the second detecting portion detects the optical connection of the second light source emission end portion and the second light guide incidence end portion, and the third detecting portion detects the optical connection of the first irradiation module or the third irradiation module and the first light guide emission end portion and the optical connection of the second irradiation module or the third irradiation module and the second light guide emission end portion.

11. The intermediary adapter according to claim 3, wherein the third adapter side connection portion comprises:

a first adapter irradiation connection portion in which the first light guide emission end portion is provided and which is mechanically connected to the first irradiation connection portion, and a second adapter irradiation connection portion in which the second light guide emission end portion is provided and which is mechanically connected to the second irradiation connection portion, and the connection of the first adapter irradiation connection portion and the first irradiation connection portion and the connection of the second adapter irradiation connection portion and the second irradiation connection portion are separately performed.

12. The intermediary adapter according to claim 2 wherein the first light guide incidence end portion is larger than the second light guide incidence end portion.

13. The intermediary adapter according to claim 2 wherein the second light guide member comprises a single optical fiber.

14. An intermediary adapter comprising:
a first adapter side connection portion which is mechanically connected to a first light source side connection portion that is provided in a first light source module that emits first light source light;
a first light guide member which guides the first light source light, and
a second light source module which emits second light source light and a second light guide member which guides the second light source light;
wherein the first light source module and a first irradiation module which functions by receiving the first light source light that is guided by the first light guide member or a third irradiation module which functions by receiving the first light source light that is guided by the first light guide member are optically connected by the first light guide member,
the second light source module and a second irradiation module which functions by receiving the second light source light or the third irradiation module which functions by receiving the second light source light are optically connected by the second light guide member, and
the first irradiation module, the second irradiation module and the third irradiation module is each mechanically attachable to and detachable from the intermediary adapter and each mechanically and interchangeably connected to the intermediary adapter in a same plane of the intermediary adapter.

15. The intermediary adapter according to claim 14, further comprising a second light guide member which optically connects a light source of the second light source module to the second irradiation module or the third irradiation module, and which guides the second light source light from the light source to the second irradiation module or the third irradiation module.

16. A light source system comprising:
at least one of a first light source module which emits first light source light and a second light source module which emits second light source light;
at least one of a first irradiation module which functions by receiving the first light source light, a second irradiation module which functions by receiving the second tight source light, and a third irradiation module which functions by receiving the first light source light or the second light source light, and
the intermediary adapter according to claim 1 or claim 14.

17. The light source system according to claim 16,
when the first irradiation module is connected to the intermediary adapter, at least the first light source module is connected to the intermediary adapter,
when the second irradiation module is connected to the intermediary adapter, at least the second light source module is connected to the intermediary adapter, and
when the third irradiation module is connected to the intermediary adapter, the first light source module and the second light source module are connected to the intermediary adapter.

18. The light source system according to claim 16, wherein
the first light source module comprises a first light source which emits the first light source light, and
the first light source comprises at least one of a LED light source, an electric discharge lamp light source, and a filament type lamp light source.

19. The light source system according to claim 16, wherein
the second light source module comprises a second light source which emits the second light source light, and
the second light source comprises at least one of a laser light source and a superluminescent light source.

* * * * *